United States Patent
Schmidt

(10) Patent No.: US 9,188,265 B2
(45) Date of Patent: Nov. 17, 2015

(54) COUPLING DEVICE FOR CONNECTING A SUPPLY TUBE FOR DENTAL INSTRUMENTS WITH A SUPPLY AND CONTROL UNIT

(71) Applicant: MEDTRONIC GmbH, Usingen (DE)

(72) Inventor: Alfred Schmidt, Usingen (DE)

(*) Notice: Subject to any disclaimer, the term of this patent is extended or adjusted under 35 U.S.C. 154(b) by 229 days.

(21) Appl. No.: 13/945,340

(22) Filed: Jul. 18, 2013

(65) Prior Publication Data

US 2014/0021716 A1 Jan. 23, 2014

(30) Foreign Application Priority Data

Jul. 23, 2012 (DE) .......................... 10 2012 106 666
Mar. 25, 2013 (DE) .......................... 10 2013 103 003

(51) Int. Cl.
  *F16L 25/12* (2006.01)
  *A61C 1/00* (2006.01)
  *A61C 1/18* (2006.01)

(52) U.S. Cl.
  CPC ............... *F16L 25/12* (2013.01); *A61C 1/0061* (2013.01); *A61C 1/18* (2013.01); *Y10T 137/87153* (2015.04); *Y10T 137/87764* (2015.04)

(58) Field of Classification Search
  CPC ......... F16L 25/12; A61C 1/0061; A61C 1/18; Y10T 137/87708; Y10T 137/87764; Y10T 137/87153
  USPC ............... 137/862, 869, 594, 614, 614.06; 251/142, 149, 149.4, 149.1, 149.8, 251/149.6; 285/149.1; 174/8, 21 R, 47, 174/68.1; 439/188; 200/51.09, 51.1; 433/126, 127, 29, 28, 146, 147
  See application file for complete search history.

(56) References Cited

U.S. PATENT DOCUMENTS

| | | | | |
|---|---|---|---|---|
| 2,510,125 A * | 6/1950 | Meakin | ........................... | 174/47 |
| 2,542,536 A * | 2/1951 | Kirksey | ....................... | 439/192 |
| 2,634,311 A * | 4/1953 | Darling | ........................ | 439/191 |
| 3,032,299 A * | 5/1962 | Martin | .................... | 244/122 AH |
| 3,254,646 A * | 6/1966 | Staunt et al. | .................. | 604/114 |
| 4,080,737 A * | 3/1978 | Fleer | ............................. | 433/126 |
| 4,403,956 A * | 9/1983 | Nakanishi | ....................... | 433/29 |
| 4,431,412 A * | 2/1984 | Lares et al. | ..................... | 433/29 |
| 4,507,085 A * | 3/1985 | Mosimann et al. | ........... | 433/126 |
| 4,957,483 A * | 9/1990 | Gonser et al. | ................... | 604/30 |
| 5,501,596 A * | 3/1996 | Bailey | ............................. | 433/86 |
| 5,603,352 A * | 2/1997 | Tavor | ....................... | 137/599.11 |
| 5,762,495 A * | 6/1998 | Pinel et al. | ....................... | 433/86 |
| 5,944,520 A * | 8/1999 | Ash | ................................. | 433/84 |
| 6,159,004 A * | 12/2000 | Rosenstatter | ................... | 433/29 |

(Continued)

FOREIGN PATENT DOCUMENTS

| | | |
|---|---|---|
| DE | 2730713 | 1/1979 |
| DE | 102006051511 | 5/2008 |

(Continued)

*Primary Examiner* — Craig Schneider
*Assistant Examiner* — David Colon Morales
(74) *Attorney, Agent, or Firm* — Welsh Flaxman & Gitler LLC

(57) ABSTRACT

The invention relates to a coupling device for connecting a supply tube for dental instruments with a supply and control unit having a coupling sleeve in which a first coupling body and a second coupling body are at least partially received along the longitudinal axis (LA) of the coupling sleeve, the first and second coupling body have several fluid ducts and electrical plug connections. The coupling device is preferably constructed in the form of a switchable valve coupling.

24 Claims, 4 Drawing Sheets

(56) References Cited

U.S. PATENT DOCUMENTS

| | | | |
|---|---|---|---|
| 7,316,424 B2 * | 1/2008 | Kardeis et al. | 285/91 |
| 7,658,205 B1 * | 2/2010 | Edelman et al. | 137/614.04 |
| 2002/0117849 A1 * | 8/2002 | Bailey | 285/123.15 |
| 2007/0248934 A1 * | 10/2007 | Mosimann | 433/126 |

FOREIGN PATENT DOCUMENTS

| | | |
|---|---|---|
| EP | 1486180 | 12/2004 |
| WO | WO01/54611 | 8/2001 |

\* cited by examiner

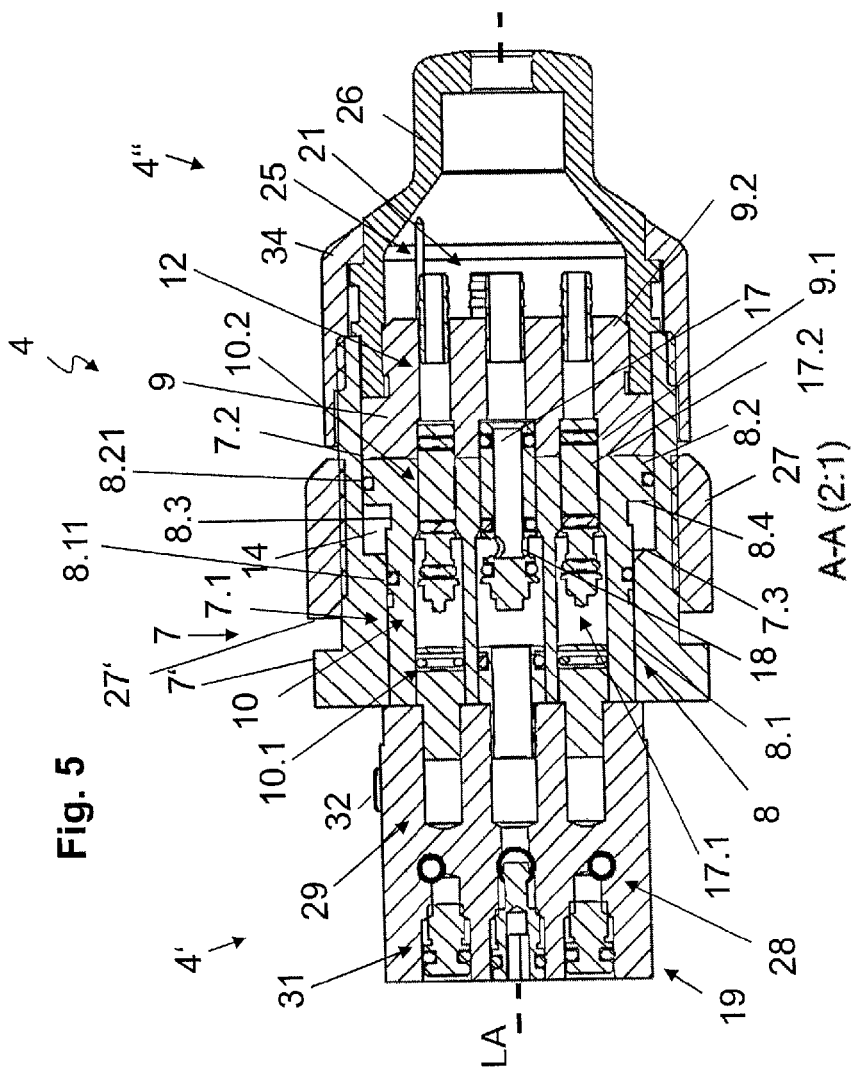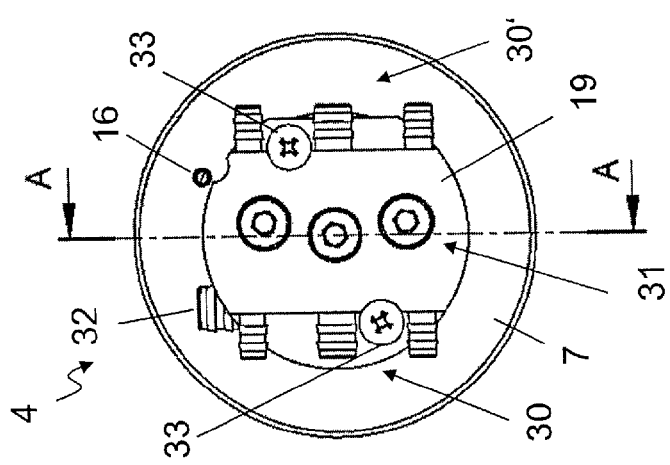

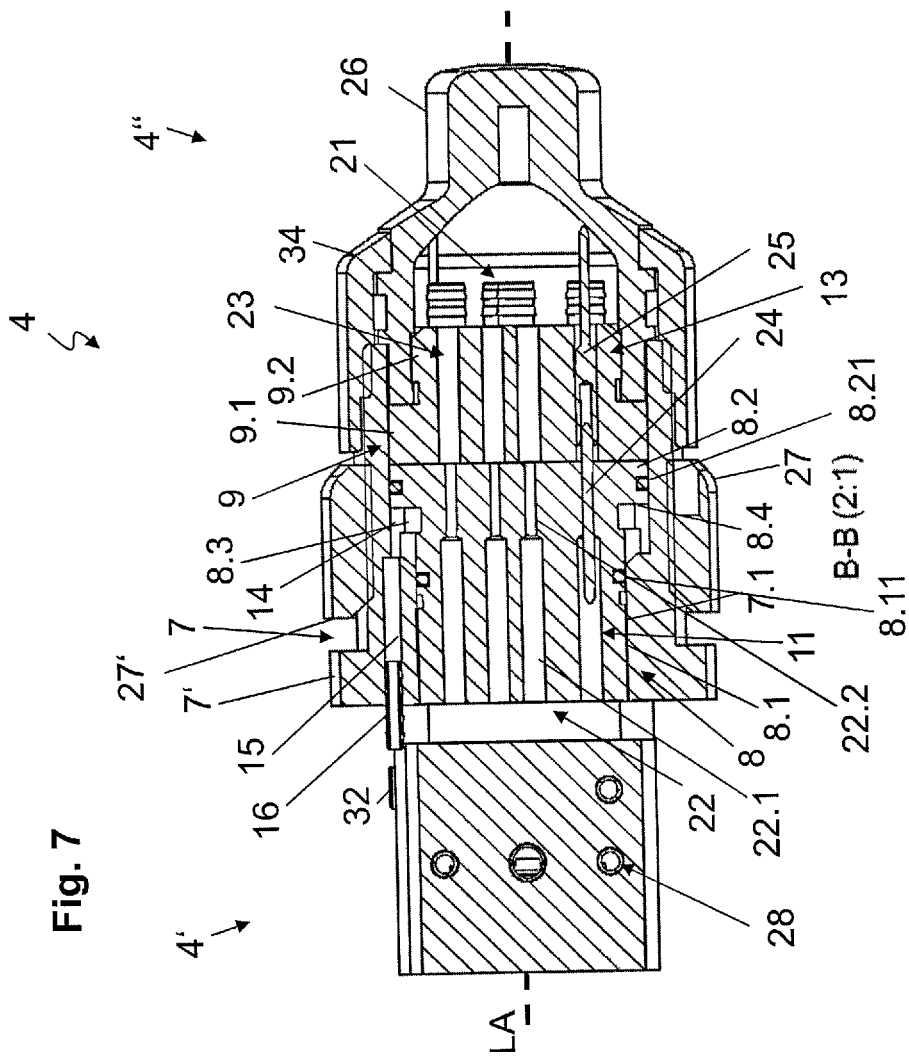
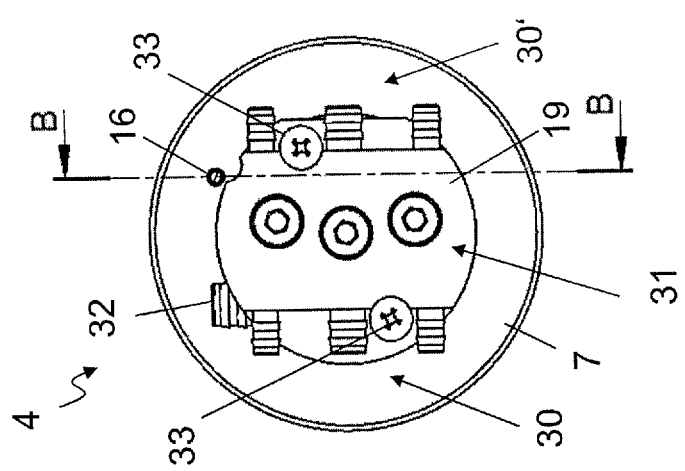

COUPLING DEVICE FOR CONNECTING A SUPPLY TUBE FOR DENTAL INSTRUMENTS WITH A SUPPLY AND CONTROL UNIT

BACKGROUND OF THE INVENTION

1. Field of the Invention

The invention relates to a coupling device for connecting a supply tube (6) for dental instruments (5) with a supply and control unit (2) comprising a coupling sleeve (7), in which a first coupling body (8) and a second coupling body (9) are at least partially received along the longitudinal axis (LA) of the coupling sleeve (7), and wherein the first and second coupling body (8, 9) have several fluid ducts and electrical plug connections.

2. Problem Solved

For the connection of dental instruments, in particular electrically and/or pneumatically operated dental instruments, coupling devices are known for connecting the respective dental instrument with a supply and control unit via a supply tube. A dental instrument usually consists of a handpiece part and a treatment implement received therein, for example, in the form of a drill. A dental instrument is also understood to mean a scale remover, such as one that operates by ultrasonic technology, or a flushing instrument. The dental instruments have in their respective handpiece part electrically or pneumatically operated motor units, or ultrasonic units, which are supplied by means of the supply tube from the supply and control unit with the fluids, electrical energy and/or electrical control signals necessary for operation.

Coupling devices can be provided both at the end on the control side associated with the supply and control unit, and also at the end of the supply tube on the instrument side.

It is also desirable to provide the compressed air necessary for driving a dental instrument precisely when this is necessary for the operation of the implement. Also, in known pneumatically operated supply and control units, which operate several dental implements, preferably having different functions, a complex pneumatic control and associated cabling are necessary, which is supplemented if applicable by electronic control components. Of particular importance is a proper operation of the supply and control unit and of the connected dental implements. In particular, it is desirable that only the dental implement which is currently in use is ready for operation, and the remaining dental implements, which are held in the supply and control unit by means of corresponding mountings, are switched off.

It is therefore an object of the invention to provide a coupling device for connecting a dental supply tube with a supply and control unit, which enables a controlled feeding of at least one fluid, electrical energy and control signals.

SUMMARY OF THE INVENTION

An essential aspect, according to the invention, is that the coupling device is constructed in the form of a switchable valve coupling. For this, the first coupling body forms a valve piston body guided in the coupling sleeve. The valve piston body is axially displaceable by being acted upon by compressed air. The second coupling body is fixedly received in the coupling sleeve. Particularly advantageous, through the realization of the coupling device according to the invention as a switchable valve coupling, is the feeding of compressed air, or switching air from a non-connected-through state into an opened or connected state. This switching action is done without great effort using the inventive control technology.

In an advantageous alternate embodiment of the invention, first fluid ducts are provided in the first coupling body and second fluid ducts are provided in the second coupling body. The first and second fluid ducts extend, respectively, along the longitudinal axes of the coupling bodies on the same axis with respect to one another. Rod-shaped valve pistons (17) with a first and second valve piston section are received, respectively, partially in the first and second fluid ducts.

Furthermore, in the non-connected-through operating state of the coupling device, the first coupling body is arranged spaced apart from the second coupling body in the coupling sleeve, wherein the first coupling body is held in this position by being acted upon by a pre-stressing. In the wall of the coupling sleeve on the control side, a bore is provided for the feeding of the compressed air or control air into an annular valve chamber enclosed by the coupling sleeve and the first coupling body. The bore extends along the longitudinal axis from the front side of the coupling sleeve, on the control side, to the annular valve chamber.

According to an advantageous further development of the invention, the rod-shaped valve piston has an inner bore which extends along the longitudinal axis of the piston, and proceeding from an inlet bore, running transversely to the longitudinal axis of the piston, with two opposite inlet openings and with an outlet opening on the front side. A first valve piston section, having the two lateral inlet openings, is received at least partially in a fluid duct of the first coupling body, and a second valve piston section, having the outlet opening on the front side, is received at least partially in the fluid duct of the second coupling body which is arranged on the same axis. The inlet openings of the first valve piston section are freed or are closed in a fluid-tight manner depending on the piston position of the first coupling body, constructed as valve piston body.

The first fluid ducts, provided in the first coupling body, have a first duct section and a second duct section adjoining directly thereon, wherein the internal diameter of the first duct section is selected to be greater than the internal diameter of the second duct section. In the non-connected-through operating state, the inlet openings of the first valve piston section are situated in the region of the second duct section and are thereby closed. In the opened or respectively connected-through operating state, the inlet openings of the first valve piston section are situated in the region of the first duct section and are thereby freed. The rod-shaped valve piston is received here with its second valve piston section securely in location or securely in position in the respectively second fluid duct of the second coupling body.

According to a further development of the invention, to produce the electrical plug connections, the first and second coupling bodies have first and second bores, arranged on the same axis, running parallel to the first and second fluid ducts, wherein in a first bore, a contact pin element, and in an opposite second bore, on the same axis, a contact bushing element, are arranged.

The second coupling body has a first and second coupling body section with different external diameters. In particular, the external diameter of the first coupling body section is greater than that of the second coupling body section, wherein the first coupling body section is guided in the coupling sleeve.

In a further development of the invention, an adapter coupling element, on the tube side, adjoins the second coupling body on the tube side. The adapter coupling element is preferably part of the supply tube. In addition, the coupling sleeve comprises a circumferential edge section and a sleeve section, reduced in cross-section, adjoining thereto. The sleeve section has on the outer surface, a screw thread, onto which a nut element is able to be screwed. Adjoining the nut element along the longitudinal axis in the direction of the connection region on the tube side is a fastening bush, which is able to be screwed onto the external thread of the coupling sleeve.

A connection adapter element, arranged on the control side, can also be provided, via which at least the feeding of the fluids takes place into the first fluid ducts of the first coupling body forming a valve piston. The connection adapter element has lead-through ducts running perpendicular to the longitudinal axis, which are connected with feed ducts running parallel to the longitudinal axis, which are arranged on the same axis and position to the first fluid ducts of the first coupling body. In the region of the intersection points of the lead-through ducts and feed ducts, dosing means are provided, via which the feeding quantity of the respectively fed fluid is able to be adjusted.

In a preferred alternate embodiment, provision is made that at least three first fluid ducts are integrated in the first coupling body and at least three second fluid ducts are integrated in the second coupling body for the leading through of water, driving-air and blowing-air through the coupling device.

In addition, further developments, advantages and possibilities for application of the innovation will also emerge from the following description of example embodiments and from the figures.

BRIEF DESCRIPTION OF THE DRAWINGS

FIG. 4 is a view on the front side of the coupling device according to the invention;
FIG. 5 is a section along the line A-A through the coupling device according to the invention in accordance with FIG. 4;
FIG. 6 is a view on the front side of the coupling device according to the invention;
and
FIG. 7 is a section along the line B-B through the coupling device according to the invention in accordance with FIG. 6.

DETAILED DESCRIPTION OF THE INVENTION

Figure 1:
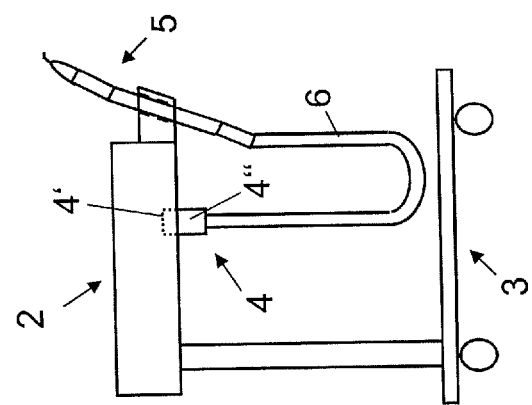
FIG. 1 is a diagrammatic side view of a dental device.

In FIG. 1, by way of example, a dental device 1 is illustrated, which has at least one supply and control unit 2. The supply and control unit 2 is constructed for the controlled provision of at least one fluid, electrical energy and/or control signals.

A dental device 1 can comprise, for example, a movable trolley 3, on which the supply and control unit 2 is arranged. Alternatively, the dental device 1 can also be part of a dental treatment unit, which is arranged, for example, so as to be pivotally and/or vertically adjustable on a treatment chair unit (not illustrated in the figures).

A dental instrument 5 is able to be connected to the supply and control unit 2 via a coupling device 4 according to the invention, and, namely, via a supply tube 6. Proceeding from the coupling device 4, a line connection, for the transmission of several fluids, electrical energy and/or control signals to the dental instrument 5, is produced by means of the supply tube 6. Preferably, a dental apparatus 1 has several dental instruments 5, which are connected to the supply and control unit 2 via a supply tube 6 and a coupling device 4. In FIG. 1, by way of example, to explain the basic structure of a coupling device 4 according to the invention, only one dental instrument 5 is illustrated, connected to the supply and control unit 2.

A dental instrument 5 is understood to be, for example, a handpiece unit with a treatment implement received exchangeably therein, a scale remover operated by ultrasonic technology, a spray gun, and/or a suction instrument. For the operation of such dental instruments 5, frequently different fluids, electrical energy and/or control signals are necessary. Preferably, the fluids, blowing-air and driving-air, an electrical supply voltage and/or electrical or pneumatic control signals, are provided by the supply and control unit 2. The supply tube 6 has in itself several tubes and electrical connection cables, via which the fluids, the electrical energy and the control signals provided by means of the coupling device 4 are transmitted to the dental instrument 6.

Figure 2:
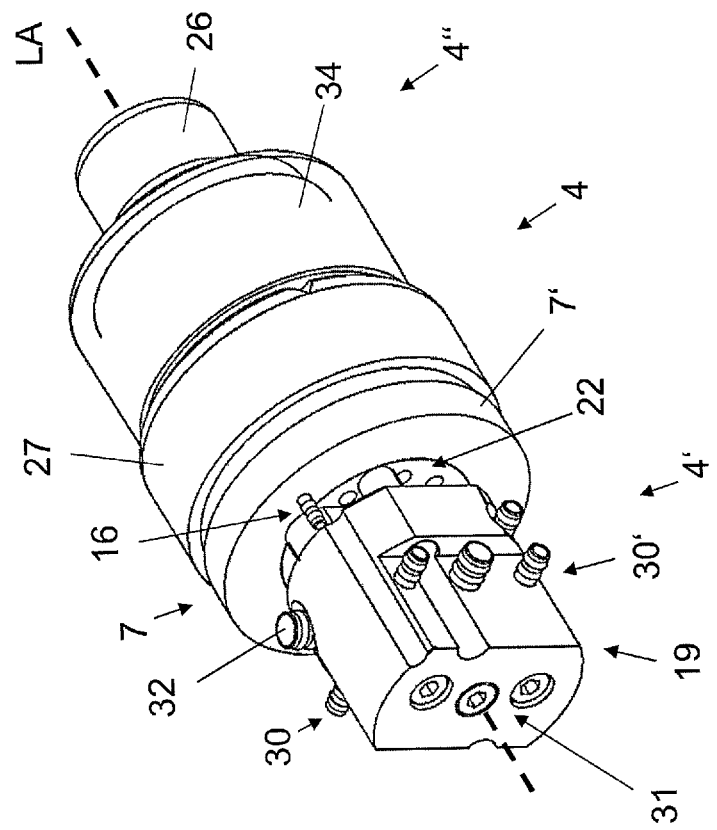
FIG. 2 is a perspective view of a coupling device according to the invention.
Figure 3:
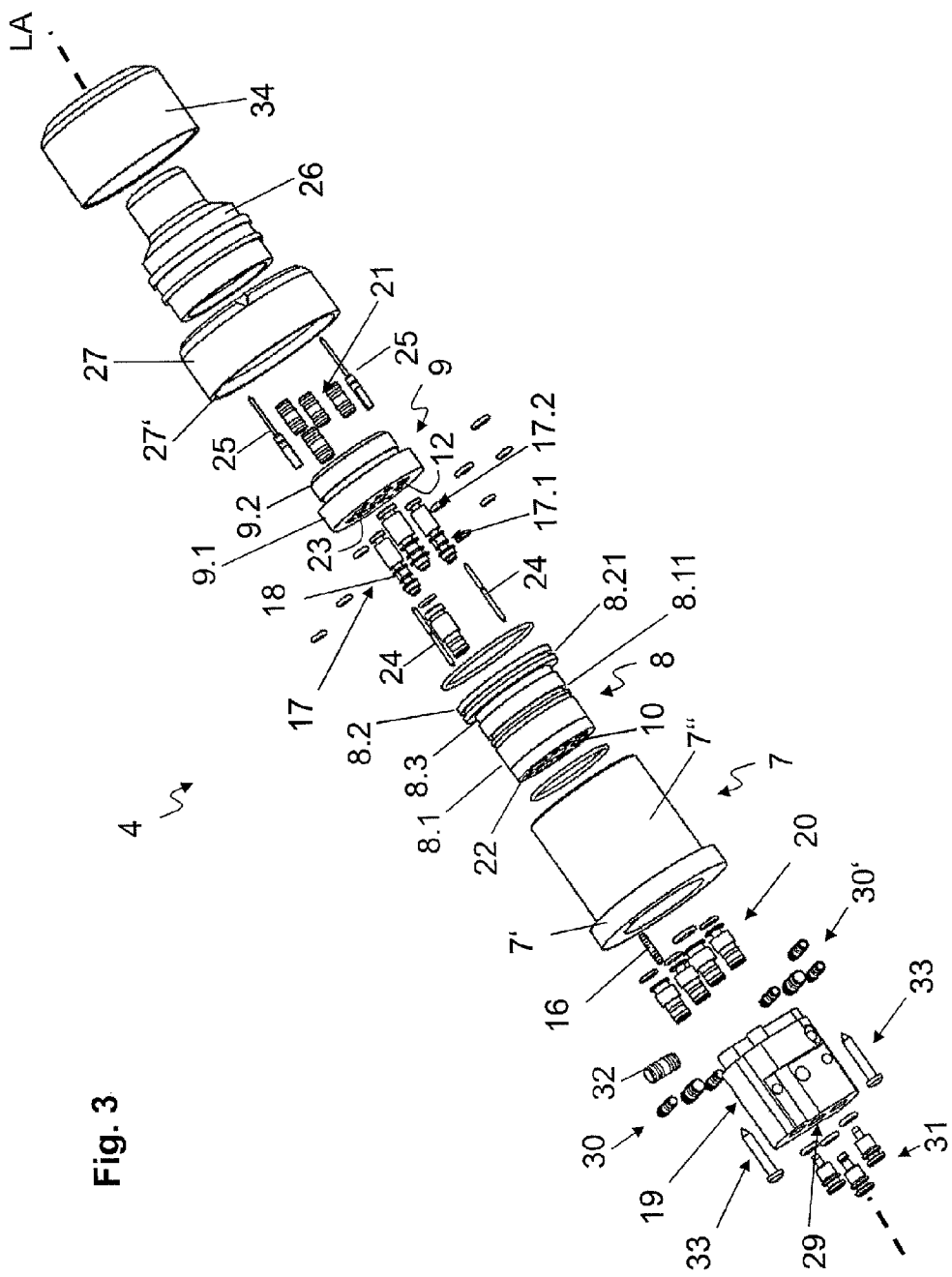
FIG. 3 is an exploded illustration of the coupling device according to the invention in accordance with FIG. 2.

FIG. 2 shows, by way of example, a perspective illustration of a coupling device 4 according to the invention, and FIG. 3 shows an associated exploded illustration. The coupling device 4 has a connection region 4' on the control side and a connection region 4" on the tube side, wherein after completed mounting of the coupling device 4 the connection region 4' on the control side is situated inside the housing of the supply and control unit 2, and the connection region 4" on the tube side is situated outside the housing of the supply and control unit 2.

The coupling device 4 comprises at least one coupling sleeve 7, in which at least partially a first coupling body 8 and partially a second coupling body 9 are received along the longitudinal axis LA of the coupling sleeve 7 or respectively of the coupling device 4, wherein the first coupling body 8 has several first fluid ducts 10 and first electrical plug connections 11, and the second coupling body 9 has several second fluid ducts 12 and second electrical plug connections 13.

According to the invention, the coupling device 4 forms a switchable valve coupling by means of which the fluid ducts 10, 12 and the electrical plug connections 11, 13 are able to be connected through at the same time. The coupling device 4 is switchable here by being acted upon with compressed air, i.e. is able to be switched over from a first operating state, in which no conducting connection exists between the fluid ducts 10, 12 and the electrical plug connections 11, 13 between the first and second coupling bodies 8, 9, into a second operating state, in which corresponding connections are connected through.

For this, the first coupling body 8 is received in the coupling sleeve 7 displaceably axially and along the longitudinal axis LA of the coupling device 4 or of the coupling sleeve 7. The first coupling body 8 is guided axially through the coupling sleeve 7 and is provided in the connection region 4' of the coupling device 4 on the control side. The second coupling body 9 adjoins the first coupling body 8 along the longitudinal axis LA in the direction of the connection region 4" on the tube side and in the mounted state is received securely in location or securely in position in the coupling sleeve 7. When the coupling device 4 is not connected through, the first coupling body 8 is arranged spaced apart from the second coupling body 9 in the coupling sleeve 7. In the connected-through state, the opposite front sides of the first and second coupling body 9 lie against one another.

According to the invention, the first coupling body 8 forms an axially displaceable valve piston body which is movable by being acted upon with compressed air from a first piston position into a second piston position, and vice versa.

For this, the first coupling body 8 is constructed so as to be substantially cylindrical and has a first coupling body section 8.1 and a second coupling body section 8.2. In the present embodiment, the first coupling body section 8.1 has an exterior circumferential groove 8.3 in the edge section adjoining the second coupling body section 8.2. The first and second coupling body section 8.1, 8.2 have different external diameters and thereby form a graduated cylinder surface, and namely such that the second coupling body section 8.2 forms an annular edge section protruding radially outwards from the longitudinal axis LA, with an annular lateral stop surface 8.4 oriented in the direction of the first coupling body section 8.1.

To form an annular valve chamber 14, the coupling sleeve 7 has a graduated inner surface course along the longitudinal axis LA. This is formed by a first and second coupling sleeve section 7.1, 7.2 adjoining one another along the longitudinal axis LA, wherein the first coupling sleeve section 7.1 has a smaller internal diameter than the second coupling sleeve section 7.2. Here, the internal diameter of the first coupling sleeve section 7.1 is adapted to the external diameter of the first coupling body section 8.1, and the internal diameter of the first coupling sleeve section 7.2 is adapted to the external diameter of the second coupling body section 8.2. Therefore, in the transition region between the first and second coupling sleeve section 7.1, 7.2 an annular stop surface 7.3 is produced, against which the second coupling body section 8.2 of the first coupling body 8 or respectively the annular lateral stop surface 8.4 rests in the first piston position.

The annular valve chamber 14 is therefore formed by the stepped inner surface section of the coupling sleeve 7 and the stepped outer surface section, including the groove 8.3, of the first coupling body 8. Both the first and the second coupling body section 8.1, 8.2 have a circumferential guide groove 8.11, 8.21 to receive a circumferential sealing element, preferably an O-ring. Therefore, a fluid-tight connection is produced between the outer surface of the first coupling body 8 and the inner surface of the coupling sleeve 7.

The feeding of the compressed air, or control air, takes place via a bore 15 which is guided in the wall of the coupling sleeve 7 along the longitudinal axis LA from the front side of the coupling sleeve 7, on the control side, to the annular valve chamber 14, in which bore 15 at the outlet side has a double nipple 16 provided for the connection of a pressure tube. The latter therefore forms the control air inlet of the coupling device 4.

For the controlled switching through of individual fluids, at least a portion of the first fluid ducts 10 of the first coupling body 8 is connected duct-wise with a portion of the second fluid ducts 12 of the second coupling body 9, and via a rod-shaped valve piston 17. The rod-shaped valve piston 17 has an inner bore which extends along the longitudinal axis of the piston, and proceeds from an inlet bore 18 running transversely to the longitudinal axis of the piston with two opposite inlet openings and an outlet opening on the end side. The first valve piston section 17.1 having the two lateral inlet openings is received here in a fluid duct 10 of the first coupling body 8 and the second valve piston section 17.2 having the outlet opening on the front side is received in the fluid duct 12 of the second coupling body arranged on the same axis.

Depending on the piston position of the first coupling body 8, constructed as valve piston body, the inlet openings of the first valve piston section 17.1 are freed or are closed in a fluid-tight manner, and thereby the provision of the fluid via the associated fluid ducts 10, 12 is controlled. To realize this, the fluid ducts 10 provided in the first coupling body 8 have a first duct section 10.1 and a second duct section 10.2 adjoining directly thereto, wherein the internal diameter of the first duct section 10.1 is selected to be greater than the internal diameter of the second duct section 10.2, so that a slanted, step-like course of the duct inner surface is produced. In the first piston position, the inlet openings of the first valve piston section 17.1 are situated in the second duct section 10.2 and are sealed with respect to the duct inner surface of the second duct section 10.2 by means of two sealing elements, preferably O-rings, enclosing the inlet openings, received in circumferential guide grooves.

In the second piston position, the inlet openings of the first valve piston section 17.1 come to lie in the region of the first duct section 10.1 and are freed owing to the greater internal diameter, so that a fluid which is fed via the first fluid duct 10 of the first coupling body is guided via the inlet openings into the inner bore 18 to the outlet opening of the second valve piston section 17.2 and finally via the further second fluid duct 12 of the second coupling body 9 arrives at the connection region 4" on the tube side. For the connection of connecting tubes or of a connection adapter element 19, the openings of the first fluid ducts 10 of the first coupling body 8 on the control side are provided with connecting nipple elements 20. The valve piston 17 is received with its second valve piston section 17.2 securely in location or securely in position in the respective second fluid duct 12 of the second coupling body 9.

Preferably, a spring element (not illustrated in the figures) is provided between a connecting nipple element 20 received on the control side in a first fluid duct 10 and the first valve piston section 17.1 of the rod-shaped valve body 17, situated therein, by means of which spring element an axially-acting pre-stressing is built up via the valve piston 17, received securely in location or securely in position in the second coupling body 9, between the first and second coupling body 8, 9. By means of the pre-stressing, the first coupling body 8, constructed as valve piston body, is held in the first piston position without being acted upon by control air, i.e. the second coupling body section 8.2 of the first coupling body 8 lies on the edge side against the stop surface 7.3 of the coupling sleeve 7. On the feeding of control air, the first coupling body 8 is displaced against the pre-stressing axially into the second piston position, and against the front face, facing the first coupling body 8, of the second coupling body 9.

In addition, in the openings of the second fluid ducts 12 of the second coupling body 9 on the tube side, connecting nipple elements 21 are received, in order to enable the connection of connecting tubes. In the present embodiment, three first fluid ducts 10 are provided in the first coupling body 8 and three second fluid ducts 12 are provided in the second coupling body 9, via which water, driving-air and blowing-air is guided through the coupling device 4. In addition, a further fluid duct is provided respectively in the first and second coupling body 8, 9, which has no valve piston 17, but rather which are connected with one another via a connecting nipple element. This continuous, non-switchable further fluid duct is provided for the returning of air from the dental implement 5 via the supply tube 6.

To produce the electrical plug connections 11, 13, the first and second coupling body 8, 9 have in addition first and second bores 22, 23 running parallel to the first and second fluid ducts 10, 12 arranged on the same axis. Here, respectively in the first bore 22, a contact pin element 24 is arranged and in the opposite second bore 22, on the same axis, a contact bushing element 25 is provided for the technical realization of the plug connection 11, 13.

In a preferred variant embodiment according to FIG. 7, the first bores 22 have a first bore section 22.1 on the control side and a second bore section 22.2 adjoining thereon, wherein the diameter of the first bore 22 is selected to be smaller in the second bore section 22.2 than in the first bore section 22.1. The contact pin element 24 is held in the second bore section 22.2 and projects by the one free end into the first bore section 22.1 and protrudes by the opposite other free end from the front face of the first coupling body outwards in the direction of the longitudinal axis LA, forming the plug section of the plug connection 11, 13.

The opposite second bore 23 extends along the longitudinal axis LA and has the same diameter throughout, wherein the latter coincides with the diameter of the first bore section 22.1 of the first bore 22 and is constructed to receive the contact bushing element 25. In the present alternate embodiment, the contact bushing element 25 has a pin-like end by which it protrudes from the front side of the second coupling body 9 on the tube side in the direction of the longitudinal axis LA and therefore forms a contact plug for the connection of a contact bushing. In an analogous manner to this, into the first bore section 22.1 a socket with an electrical conductor connected thereto for the production of an electrically conducting connection with the contact pin element 24 can be introduced on the control side into the first bore section 22.1, wherein the electrical conductor is guided via the first bores 22 to the respective contact pin element 24.

For the connection of the supply tube 6 or of the tubes and electrical connection cables received therein to the coupling device 4, an adapter coupling element 26 on the tube side adjoins the second coupling body 9 in the coupling device 4 on the tube side. The adapter coupling element 26 is preferably part of the supply tube 6. This element 26 able to be fitted onto the end of the second coupling body 9 on the tube side, such that it is received still partially by the coupling sleeve 7 at least on the free end side. For this, the second coupling body 9, in the alternate embodiment illustrated in FIGS. 3, 5 and 7, has for a first and second coupling body section 9.1, 9.2, different diameters. The external diameter of the first coupling body section 9.1 is greater than the diameter of the second coupling body section 9.2, wherein the first coupling body section 9.1 is guided in the coupling sleeve 7 and the second coupling body section 9.2 is dimensioned, as regards to its external diameter, such that a clamping mounting takes place of the adapter coupling element 26 between the outer surface of the second coupling body section 9.2 and the inner surface of the free end of the coupling sleeve 7.

The coupling sleeve 7 connecting the first and second coupling body 8, 9 with one another has at the end on the control side an axially outwardly protruding circumferential edge section 7', which forms a lateral annular stop face against which the housing of the supply and control unit 2 lies. Adjoining the circumferential edge section 7' is a sleeve section 7" of reduced cross-section, which preferably has a screw thread on the outer surface. A nut element 27 is able to be screwed onto the screw thread. Thereby, a clamping fastening of the coupling device 4 is possible in a circular recess of the housing wall, or suchlike flat fastening surface, of the supply and control unit 2. The fastening takes place by screwing the nut element 27 with the coupling sleeve 7, so that a force fit is produced between the edge region 7' of the coupling sleeve 7 and the edge region 27' of the nut element 27.

A fastening bush 34 adjoins the nut element 27 along the longitudinal axis LA in the direction of the connection region 4" on the tube side. The fastening bush 34 is also able to be screwed onto the external thread of the coupling sleeve 7. The fastening bush 34 receives the adapter coupling element 26 by screwing with the coupling sleeve 7. The adapter coupling element 26 is pressed onto the free end of the coupling sleeve 7 on the front side, and a clamping connection is produced between the second coupling body 9, the adapter coupling element 26 and the reduced sleeve section 7" of the coupling sleeve 7 on the tube side.

In a preferred variant embodiment of the invention, the coupling device 4 has a connection adapter element 19, whereby the feeding of the fluids takes place into the first fluid ducts 10 of the first coupling body 8 forming a valve piston. In FIGS. 2 to 7, by way of example a realization of such a connection adapter element 19 is illustrated.

In the present alternate embodiment, the connection adapter element 19 has three lead-through ducts 28 running perpendicular to the longitudinal axis LA. At the opposite openings of the lead-through ducts connection nipples 30, 30' are at least partially received therein. The lead-through ducts 28 run perpendicular to the longitudinal axis LA and are connected with the feed ducts 29 which run parallel to the longitudinal axis LA. They are arranged for connection with the connecting nipple elements 20 of the first coupling body 8 on the same axis and position to the first fluid ducts 10.

The fluids, driving-air and blowing-air are guided via the lead-through ducts 28 to the feed ducts 29, wherein here preferably in the region of the intersection points of the lead-through ducts and the feed ducts 28, 29. Dosing means 31 can be provided, via which the feeding quantity, of the fluids, are able to be adjusted.

Finally, the connection adapter element 19 also has an outlet nipple 32, which is able to be connected via a further feed duct (not illustrated in the figures) with the further fluid duct provided in the first coupling body 8.

The connection adapter element 19 is securely connected with the front side of the first coupling body 8 on the control side by means of detachable connecting means, such as screws 33.

The invention was described above in a representative embodiment. It shall be understood that numerous modifications and alterations to the invention are possible, without hereby departing from the inventive idea.

LIST OF REFERENCE NUMBERS 1 dental device
2 supply and control unit
3 movable trolley
4 coupling device
4' connection region on the control side
4" connection region on the tube side
dental instrument
6 supply tube
7 coupling sleeve
7' edge region
7" reduced sleeve region
7.1 first coupling sleeve section
7.2 second coupling sleeve section
7.3 annular stop surface
8 first coupling body
8.1 first coupling body section
8.11 guide groove
8.2 second coupling body section
8.21 guide groove
8.3 outer circumferential groove
8.4 annular stop surface
9 second coupling body
9.1 first coupling body section
9.2 second coupling body section
10 first fluid ducts
10.1 first duct section
10.2 second duct section
11 first electrical plug connections
12 second fluid ducts
13 second electrical plug connections
14 annular valve chamber
15 bore 16 double nipple
17 rod-shaped valve piston
17.1 first valve piston section
17.2 second valve piston section
18 inlet bore
19 connection adapter element
20 connecting nipple elements
21 connecting nipple elements
22 first bores
23 second bores
24 contact pin element
25 contact bushing element
26 adapter coupling element
27 nut element
27' edge region
28 lead-through ducts
29 feed ducts
30, 30' connection nipple
31 dosing means
32 outlet nipple
33 screws
34 fastening bush
LA longitudinal axis

What is claimed is:

1. A coupling device for connecting a supply tube for dental instruments with a supply and control unit, the coupling device comprising:
a coupling sleeve in which a first coupling body and a second coupling body are at least partially received along a longitudinal axis (LA) of the coupling sleeve, wherein the first coupling body and the second coupling body comprise several fluid ducts and electrical plug connections, wherein the coupling device is a switchable valve coupling, and wherein the first coupling body comprises a valve piston body guided in the coupling sleeve, and wherein the valve piston body is displaceable axially by being acted upon with compressed air.

2. The coupling device according to claim 1, wherein the second coupling body is fixedly received in the coupling sleeve.

3. The coupling device according to claim 1, further comprising first fluid ducts in the first coupling body and second fluid ducts in the second coupling body, the first fluid ducts and the second fluid ducts extend along the longitudinal axis (LA) of the first coupling body and the second coupling body on a same axis with respect to one another.

4. The coupling device according to claim 1, further comprising a rod-shaped valve piston with a first piston valve section and a second valve piston section received partially in the first fluid ducts and the second fluid ducts.

5. The coupling device according to claim 1, wherein when the coupling is in a non-connected-through operating state, the first coupling body is arranged in a spaced apart position from the second coupling body in the coupling sleeve, and wherein the first coupling body is held in the spaced apart position.

6. The coupling device according to claim 4, wherein in a wall of the coupling sleeve on a control side, a bore is provided for feeding of compressed air or control air into an annular valve chamber enclosed by the coupling sleeve and the first coupling body, the bore extends along the longitudinal axis (LA) from a front side of the coupling sleeve on the control side to the annular valve chamber.

7. The coupling device according to claim 4, wherein in that the rod-shaped valve piston has an inner bore which extends along a longitudinal axis of the piston, and extends from an inlet bore running transversely to the longitudinal axis of the piston and the rod-shaped piston valve has two opposite inlet openings and an outlet opening on a front side of the coupling device.

8. The coupling device according to claim 7, wherein the first valve piston section has two lateral inlet openings received at least partially in a fluid duct of the first coupling body and the second valve piston section has an outlet opening on the front side of coupling device and is received at least partially in a fluid duct of the second coupling body arranged on the same axis.

9. The coupling device according to claim 8, wherein depending on a piston position of the first coupling body, the first coupling body being constructed as a valve piston body, inlet openings of the first valve piston section are freed or are closed in a fluid-tight manner.

10. The coupling device according to claim 8, wherein the first fluid ducts provided in the first coupling body have a first duct section and a second duct section adjoining directly thereon, and wherein an internal diameter of the first duct section is greater than an internal diameter of the second duct section.

11. The coupling device according to claim 8, wherein in a non-connected-through operating state, inlet openings of the first valve piston section are situated in a region of the second duct section and are thereby closed.

12. The coupling device according to claim 8, wherein in a connected-through operating state, inlet openings of the first valve piston section are situated in a region of the first duct section and are thereby freed.

13. The coupling device according to claim 8, wherein the rod-shaped valve piston is received with its second valve piston section securely in location or securely in position in the second fluid duct of the second coupling body.

14. The coupling device according to claim 3, wherein for production of electrical plug connections, the first coupling body and the second coupling body have first and second bores running parallel to the first and second fluid ducts, all arranged on a same axis.

15. The coupling device according to claim 14, further comprising a contact pin element arranged in the first bore and a contact bushing element is arranged in the opposite second bore on the same axis.

16. The coupling device according to claim 1, wherein the second coupling body has a first coupling body section and a second coupling body section with different external diameter.

17. The coupling device according to claim 16, wherein an external diameter of the first coupling body section is greater an external diameter of the second coupling body section, and wherein the first coupling body section is guided in the coupling sleeve.

18. The coupling device according to claim 1, further comprising an adapter coupling element on a tube side adjoins the second coupling body on the tube side, and the adapter coupling element is part of the supply tube.

19. The coupling device according claim 1, wherein the coupling sleeve has a circumferential edge section and a sleeve section reduced in cross-section adjoining thereon, the sleeve section has a screw thread on the outer surface onto which a nut element is able to be screwed.

20. The coupling device according to claim 19, further comprising a fastening bush adjoining the nut element along the longitudinal axis (LA) in a direction of a connection region on a tube side, and the fastening bush is able to be screwed onto an external thread of the coupling sleeve.

21. The coupling device according to claim 1, further comprising a connection adapter element arranged on a control side of the coupling device by which feeding of fluids takes place into first fluid ducts of the first coupling body forming a valve piston.

22. The coupling device according to claim 21, wherein the connection adapter element has lead-through ducts running perpendicular to the longitudinal axis (LA), which are connected with feed ducts running parallel to the longitudinal axis (LA), and the feed ducts are arranged on a same axis and position to the first fluid ducts of the first coupling body.

23. The coupling device according to claim 22, wherein in a region of an intersection points of the lead-through ducts and feed ducts, adjustable dosing means are provided for feeding a quantity of fluid.

24. The coupling device according to claim 1, further comprising at least three first fluid ducts provided in the first coupling body and at least three second fluid ducts provided in the second coupling body for the leading through of fluids, driving-air and blowing-air through the coupling device.

* * * * *